(12) United States Patent
Schreibmann et al.

(10) Patent No.: US 8,774,481 B2
(45) Date of Patent: Jul. 8, 2014

(54) ATLAS-ASSISTED SYNTHETIC COMPUTED TOMOGRAPHY USING DEFORMABLE IMAGE REGISTRATION

(75) Inventors: Eduard Schreibmann, Atlanta, GA (US); Tim Fox, Atlanta, GA (US)

(73) Assignee: Emory University, Atlanta, GA (US)

( * ) Notice: Subject to any disclaimer, the term of this patent is extended or adjusted under 35 U.S.C. 154(b) by 619 days.

(21) Appl. No.: 13/072,144

(22) Filed: Mar. 25, 2011

(65) Prior Publication Data

US 2011/0235884 A1 Sep. 29, 2011

Related U.S. Application Data

(60) Provisional application No. 61/317,401, filed on Mar. 25, 2010.

(51) Int. Cl.
*G06K 9/00* (2006.01)
*A61B 6/00* (2006.01)

(52) U.S. Cl.
USPC ............................................. 382/131; 378/4

(58) Field of Classification Search
None
See application file for complete search history.

(56) References Cited

U.S. PATENT DOCUMENTS

| | | | | |
|---|---|---|---|---|
| 5,568,384 A | * | 10/1996 | Robb et al. | 715/202 |
| 5,633,951 A | * | 5/1997 | Moshfeghi | 382/154 |
| 5,951,475 A | * | 9/1999 | Gueziec et al. | 600/425 |
| 5,956,418 A | * | 9/1999 | Aiger et al. | 382/154 |
| 6,154,518 A | * | 11/2000 | Gupta | 378/62 |
| 6,266,453 B1 | * | 7/2001 | Hibbard et al. | 382/294 |
| 6,996,261 B2 | * | 2/2006 | deCharms | 382/131 |
| 7,259,762 B2 | * | 8/2007 | Tanacs et al. | 345/424 |
| 7,483,034 B2 | * | 1/2009 | Chefd'hotel et al. | 345/582 |
| 7,486,811 B2 | * | 2/2009 | Kaufman et al. | 382/128 |
| 7,570,791 B2 | * | 8/2009 | Frank et al. | 382/132 |
| 7,609,884 B1 | * | 10/2009 | Stalling et al. | 382/168 |
| 7,616,835 B2 | * | 11/2009 | Lobregt | 382/294 |
| 7,778,488 B2 | | 8/2010 | Nord | |
| 7,783,132 B2 | * | 8/2010 | Nowinski et al. | 382/294 |
| 2009/0228299 A1 | | 9/2009 | Kangarloo | |
| 2009/0263000 A1 | | 10/2009 | Shinagawa | |
| 2010/0166276 A1 | | 7/2010 | Dube | |

OTHER PUBLICATIONS

Chen M et al: "Anomaly detection through registration", Pattern Recognition, Elsevier, GB, vol. 32, No. 1, Jan. 1, 1999, pp. 113-128, XP004151618, ISSN: 0031-3203, DOI: DOI: 10.1016/S0031-3203(98) 00094-6.

Hofmann Matthias et al: "MRI-Based Attenuation Correction for PET/MRI: A Novel Approach Combining Pattern Recognition and Atlas Registration",Journal of Nuclear Medicine, Society of Nuclear Medicine, Reston, VA, US, vol. 49, No. 11, Nov. 1, 2008, pp. 1875-1883, XP007908997, ISSN: 0161-5505, DOI: DOI:10.2967/JNUMED.107.049353.

(Continued)

*Primary Examiner* — Manav Seth
(74) *Attorney, Agent, or Firm* — Thomas|Horstemeyer, LLP

(57) ABSTRACT

Disclosed are systems for and methods of creating a synthetic image by registering a reference or atlas image to a clinical image using both rigid and deformable image registration algorithms. In some embodiments, a synthetic computed tomography (CT) image may be created by registering an atlas CT image to a clinical image such as an MR scan. Rigid registration in some embodiments may be followed by a smoothing B-spline transform algorithm with a mutual information similarity metric and an optimizer; followed then by an image signal intensity algorithm with displacement vectors at each voxel and diffeomorphic transformations.

25 Claims, 10 Drawing Sheets

(56) References Cited

OTHER PUBLICATIONS

Thomas Beyer et al: "MR-based attenuation correction for torso-PET/MR imaging: pitfalls in mapping MR to CT data", European Journal of Nuclear Medicine and Molecular Imaging, Springer, Berlin, DE, vol. 35, No. 6, Feb. 19, 2008, pp. 1142-1146,XP019624135, ISSN: 1619-7089.

Lester H et al: "A survey of hierarchical non-linear medical image registration",Pattern Recognition, Elsevier, GB, vol. 32, No. 1, Jan. 1, 1999, pp. 129-149,XP004151619, ISSN: 0031-3203, DOI: DOI: 10.1016/S0031-3203 (98)00095-8.

"European Search Report", Dated Aug. 5, 2011 for European Patent Application No. 11159893.4.

Shackleford et al.; On Developing B-spline Registration Algorithms for Multi-core Processors; Physics in Medicine and Biology; Oct. 2010; pp. 6329-6351; vol. 55; Institute of Physics and Engineering in Medicine.

Schreibmann et al.; MR-based Attenuation Correction for Hybrid PET-MR Brain Imaging Systems Using Deformable Image Registration; Medical Physics; May 2010; pp. 2101-2109; vol. 37, No. 5, American Association of Physicists in Medicine.

Judenhofer et al.; Simultaneous PET-MRI: A New Approach for Functional and Morphological Imaging; Nature Medicine; Mar. 2008; pp. 459-465; vol. 14; Nature Publishing Group.

Catana et al.; Simultaneous In Vivo Positron Emission Tomography and Magnetic Resonance Imaging; Proceedings of the National Academy of Science; 2008; pp. 3705-3710; vol. 105.

Lawson, et al.; Quantitative Evaluation of Cone-beam Computed Tomography—Computed Tomography (CBCT-to-CT) Deformable Image Registration Method for Adaptive Radiation Therapy; Journal of Applied Clinical Medical Physics; Fall 2007; pp. 96-113; vol. 8, No. 4.

Sharp, et al.; GPU-based Streaming Architectures for Fast Cone-Beam CT Image Reconstruction and Demons Deformable Registration; Physics in Medicine and Biology; 2007; pp. 5771-5783; vol. 52; Institute of Physics Publishing Ltd.

Vercauteren, et al.; Non-parametric Diffeomorphic Image Registration With the Demons Algorithm; Medical Image Computing and Computer-Assisted Intervention; 2007; pp. 319-326; vol. 10.

Zaidi, et al.; Is MR-guided Attenuation Correction a Viable Option for Dual-Modality PET/MR Imaging?; Radiology; Sep. 2007; pp. 639-642; vol. 244, No. 3.

Lucignani; Time-of-flight PET and PET/MRI: Recurrent Dreams or Actual Realities? European Journal of Nuclear Medicine and Molecular Imaging; Jun. 2006; pp. 969-971; vol. 33; Springer-Verlag.

Raylman et al.; Simultaneous MRI and PET Imaging of a Rat Brain; Physics in Medicine and Biology; Nov. 2006; pp. 6371-6379; vol. 51, No. 24; Institute of Physics Publishing Ltd.

Schreibmann, et al.; Image Interpolation in 4D CT Using a B-spline Deformable Registration Model; International Journal of Radiation Oncology Biology and Physics; 2006; pp. 1537-1550; vol. 64, No. 5; Elsevier Inc.

Cuadra et al.; Dense Deformation Field Estimation for Atlas-based Segmentation of Pathological MR Brain Images; Computer Methods and Programs in Biomedicine; 2006; pp. 66-75; vol. 84; Elsevier Science Inc.

DeCraene et al.; Incorporating Metric Flows and Sparse Jacobian Transformations in ITK; The Insight Journal; Mar. 2006; pp. 1-14; Release 0.10; http://hdl.handle.net/1926/1183.

Sadowsky et al.; Atlas-assisted Tomography: Registration of a Deformable Atlas to Compensate for Limited-angle Cone-beam Trajectory; IEEE International Symposium on Biomedical Imaging; Apr. 2006; pp. 1244-1247; IEEE.

Mackewn et al.; Design and Development of an MR-compatible PET Scanner for Imaging Small Animals; IEEE Transactions on Nuclear Science; Oct. 2005; pp. 1376-1380; vol. 52, Issue 5; IEEE.

Montandon et al.; Atlas-guided Non-uniform Attenuation Correction in Cerebral 3D PET Imaging; NeuroImage; 2005; pp. 278-286; vol. 25; Elsevier Inc.

Braem et al.; Feasibility of a Novel Design of High Resolution Parallax-free Compton Enhanced PET Scanner Dedicated to Brain Research; Physics in Medicine and Biology; May 2004; pp. 2547-2562; vol. 49, Issue 12; Institute of Physics Publishing Ltd.

Cuadra et al.; Atlas-based Segmentation of Pathological MR Brain Images Using a Model of Lesion Growth; IEEE Transactions on Medical Imaging; Oct. 2004; pp. 1301-1314; vol. 23, No. 10; IEEE.

Zaidi et al.; Magnetic Resonance Imaging-Guided Attenuation and Scatter Corrections in Three-Dimensional Brain Positron Emission Tomography; Medical Physics; May 2003; pp. 937-948; vol. 30, No. 5, American Association of Physicists in Medicine.

Ibanez et al.; The ITK Software Guide; Kitware Inc.; www.ITK.org (2003).

Vemuri, et al.; Image Registration Via Level-set Motion: Applications to Atlas-based Segmentation; Medical Image Analysis; 2003; pp. 1-20; vol. 7; Elsevier Science B.V.

Mattes et al.; PET-CT Image Registration in the Chest Using Free-form Deformations; IEEE Transactions on Medical Imaging; Jan. 2003; pp. 120-128; vol. 22, No. 1; IEEE.

Burger, et al.; PET Attenuation Coefficients From CT Images: Experimental Evaluation of the Transformation of CT into PET 511-keV Attenuation Coefficients; European Journal of Nuclear Medicine and Molecular Imaging; 2002; pp. 922-927; vol. 29, No. 7; Springer-Verlag.

Hermosillo et al.; Variational Methods for Multimodal Image Matching; International Journal of Computer Vision; 2002; pp. 329-343; vol. 50, No. 3; Kluwer Academic Publishers.

Hermosillo et al.; A Variational Approach to Multi-modal Image Matching; Research Report No. 4117, INRIA, Institut National de Recherche en Informatique et en Automatique; Feb. 2001.

Thirion; Image Matching as a Diffusion Process: An Analogy with Maxwell's Demons; Medical Image Analysis; 1998; pp. 243-260; vol. 2, No. 3; Oxford University Press.

Shao et al.; Simultaneous PET and MR Imaging; Physics in Medicine and Biology; May 1997; pp. 1965-1970; vol. 42, Issue 10; Institute of Physics Publishing.

Liu and Nocedal; On the Limited Memory BFGS Method for Large Scale Optimization; Mathematical Programming; 1989; pp. 503-528; vol. 45.

Lorensen et al.; Marching Cubes: A High Resolution 3D Surface Construction Algorithm; ACM SIGGRAPH; 1987; pp. 163-169; vol. 21; Association of Computing Machinery.

\* cited by examiner

ATLAS-ASSISTED SYNTHETIC COMPUTED TOMOGRAPHY USING DEFORMABLE IMAGE REGISTRATION

CROSS-REFERENCE TO RELATED APPLICATION

This application claims the benefit of U.S. Provisional Application 61/317,401, entitled "MR-Based Attenuation Correction for Hybrid PET-MR Systems Using Deformable Image Registration," filed Mar. 25, 2010, which is hereby incorporated herein by reference in its entirety.

BACKGROUND

The following disclosure relates generally to the field of medical imaging systems and, more specifically, to the application of deformable image registration techniques in a computer software tool for creating a synthetic computed tomography (CT) image.

Tomography refers to a technique for capturing a two-dimensional slice or cross-sectional image of an object, through the use of radiation or any kind of penetrating wave. The word tomography is likely derived from the Greek words, tomos (slice, section) and grapho or graphein (to write). Computed Tomography (CT) refers to a medical imaging technique that uses X-rays and computer processors to collect and display a series of two-dimensional images or tomograms of an object. Additional computer processing and mathematics can be used to generate a three-dimensional image. Magnetic Resonance (MR) imaging refers to a tomographic technique that uses a powerful magnetic field and a radio frequency transmitter to capture detailed images of organs and structures inside the body.

Positron Emission Tomography (PET) refers to an imaging technique that produces a three-dimensional image of the body. To conduct a PET scan, a short-lived radioactive tracer isotope is injected into the patient. As the isotope in the tracer decays, it emits a positron. When a positron interacts with electrons in the body, the interaction produces a pair of gamma photons. When the photons pass through the body and eventually reach a set of scintillator crystals in the scanning device, the resulting bursts of light are detected, creating an image.

Attenuation refers to the gradual loss of energy as a signal passes through a medium. In the context of Computed Tomography, attenuation of the X-ray energy occurs as the X-rays pass through different tissues and structures in the body. Similarly, for Positron Emission Tomography, attenuation of the photon energy occurs as the gamma photons pass through different tissues and structures in the body. Different tissues have different densities and, thus, produce different amounts of attenuation. The attenuation coefficient describes the extent to which a particular material or tissue causes a loss of energy.

Combination or hybrid imaging techniques are particularly useful, especially when the two images can be aligned or registered. For example, the anatomical images obtained by CT can be combined with the metabolic information shown in a PET image, to reveal both the structure of the body and its biochemical activity on a single display. The integration of PET and CT scanners in a single gantry has allowed for the simultaneous capture of both types of images. A combined PET-MR scanner has the potential to significantly change healthcare and revolutionize clinical practice because it allows the simultaneous visualization of both molecular and anatomical imaging. MR provides better soft-tissue contrast differentiation than CT. Combined PET-MR scanners can correlate temporally a PET measurement (including metabolic processes, blood flow, binding potential, distribution volume, etc.) with an MR measurement (blood flow, diffusion and perfusion, etc.) and thus create new possibilities for more specific disease assessment. Hybrid PET-MR systems will likely become the advanced imaging modality of choice for neurological studies, for the analysis of certain forms of cancer and stroke, and for the emerging study of stem cell therapy.

Image registration is the process of aligning different sets of data into a common coordinate system. The different data sets may include raw image data from different times, different viewpoints, or different types of scanning devices. Image registration allows the user to more accurately compare data from different sets. For example, the images from CT scans taken at different times, for example, can be aligned in order to identify changes occurring over time. Image registration can also be performed on data sets obtained from two different types of scans or modalities. For example, a CT image may be aligned or co-registered with an MR image, in order to display the information gathered by both scans. In mathematical terms, image registration is the process of determining the spatial transform function that maps the points in a first image to homologous points in a second image.

Segmentation is the process of identifying and classifying data found in a digitally sampled representation, such as the data acquired from a medical imaging device. Image segmentation is typically used to locate discrete objects and boundaries in the image. For example, segmentation helps identify anatomical features, locate tumors, and measure tissue volumes. The Insight Tool Kit (ITK) is an open-source software tool for performing image registration and segmentation. The ITK includes a framework of separate components, functions and routines that can be selected separately and customized by the user to assist with particular types of image registration and segmentation.

Hybrid PET-MR systems are currently in use for imaging the head and brain. Attenuation correction maps are not directly available for processing combined PET-MR data into accurate images. One of the most significant problems associated with PET imaging is photon attenuation caused by the patient's own tissues, which reduces the apparent radiopharmaceutical activity, causing image degradation, and potentially preventing the patient from receiving appropriate diagnosis or therapy. One existing protocol includes the extra step of obtaining a separate CT scan for reference, in order to use the CT dataset to obtain an attenuation correction map that can be used in the PET image reconstruction algorithms. Obtaining a reference CT scan, however, exposes the patient to an additional dose of radiation, increases health care costs, takes more time, and may introduce errors to the extent the patient changes posture or position during the additional scan procedure. There is a need, therefore, for improved systems and methods of building attenuation correction maps for hybrid imaging systems.

SUMMARY

A system for creating a synthetic computed-tomography (CT) image volume, according to various embodiments comprises: (1) a rigid registration algorithm configured to register a reference CT image volume to a first clinical image volume and thereby produce a first registration; (2) a smoothing function configured to further refine the first registration and thereby produce a smoothed registration; and (3) a voxelwise intensity algorithm configured to further refine the smoothed registration and thereby produce a synthetic CT image volume having characteristics correlated to those of the first clinical image volume. In some embodiments, the system further comprises a map of attenuation coefficients based on the synthetic CT image volume; and an attenuation correction engine configured to correct the attenuation in a second clinical image volume based on the map. In some embodiments, the rigid registration algorithm is further configured to register the first clinical image volume to each of a plurality of candidate CT image volumes and thereby obtain a plurality of corresponding candidate similarity metrics; and the system further comprises a selection tool configured to select a reference CT image volume from among the plurality of candidate CT image volumes based on a comparison of each of the plurality of corresponding candidate similarity metrics to a desired similarity metric. In some embodiments, the rigid registration algorithm comprises: (1) an affine transform algorithm having a plurality of variables including translation, rotation, scale, and shear; (2) a similarity metric representing the alignment of the reference CT image volume to the first clinical image volume; and (3) an optimizer configured to iteratively adjust the variables until the similarity metric achieves a minimum limit. In some embodiments, the optimizer further comprises: (1) an iteration maximum; (2) a similarity metric minimum; and (3) a module configured to halt the optimizing after either the iteration maximum equals about thirty or the similarity metric minimum falls below about $10^{-5}$.

In some embodiments, the smoothing function comprises: (1) a B-spline transform wherein a deformation is defined by a grid of nodes superimposed on the first registration, the transform having a plurality of variables including node deformation; (2) a similarity metric representing the alignment of the first registration to the first clinical image volume; and (3) an optimizer configured to iteratively adjust the variables until the similarity metric achieves a minimum limit. In some embodiments, the B-spline transform comprises: (1) a first stage B-spline transform wherein the grid of nodes comprises a first grid of nodes arrayed at a first spacing distance superimposed on the first registration, the first stage producing an intermediate registration; and (2) a second stage B-spline transform wherein the grid of nodes further comprises a second grid of nodes arrayed at a second spacing distance superimposed on the intermediate registration, wherein the second spacing distance is shorter than the first spacing distance.

In some embodiments, the voxelwise algorithm comprises: (1) a deformable image registration transform having a plurality of nonlinear variables; (2) a displacement vector defined at least at each voxel; (3) a similarity metric representing the alignment of the smoother registration to the first clinical image volume; (4) an optimizer configured to iteratively adjust the nonlinear variables according to the displacement vector until the similarity metric achieves a minimum limit. In some embodiments, the optimizer is further configured to iteratively adjust the nonlinear variables according to a partial differential equation having a diffeomorphic update step. In some embodiments, the similarity metric comprises a variational expression of a mutual information component that is varied according to a local value of an image intensity gradient based at least partially on the displacement vector.

A method of creating a synthetic computed-tomography (CT) image volume, according to further embodiments, comprises: (1) obtaining a first clinical image volume; (2) retrieving a reference CT image volume; (3) applying a rigid registration algorithm to register the reference CT image volume to the first clinical image volume and thereby produce a first registration; (4) applying a smoothing function to the first registration and thereby produce a smoothed registration; and (5) applying a voxelwise intensity algorithm to the smoothed registration and thereby produce a synthetic CT image volume having characteristics correlated to those of the first clinical image volume. In some embodiments, the method further comprises: (5) obtaining a second clinical image volume; (6) deriving a map of attenuation coefficients based on the synthetic CT image volume; and (7) correcting the second clinical image volume for attenuation based on the map. In some embodiments, the step of retrieving a reference CT image volume comprises: (1) establishing a desired similarity metric; (2) selecting a plurality of candidate CT image volumes; (3) executing the rigid registration algorithm to register the first clinical image volume to each of the plurality of candidate CT image volumes and thereby obtain a plurality of corresponding candidate similarity metrics; and (4) selecting the a reference CT image volume from among the plurality of candidate CT image volumes based on a comparison of each of the plurality of corresponding candidate similarity metrics to a desired similarity metric.

In some embodiments, the step of applying a rigid registration algorithm comprises: (1) executing an affine transform algorithm having a plurality of variables including translation, rotation, scale, and shear; (2) selecting a similarity metric representing the alignment of the reference CT image volume to the first clinical image volume; and (3) optimizing the variables iteratively until the similarity metric achieves a minimum limit. In some embodiments, the step of optimizing further comprises: (1) setting an iteration maximum; (2) setting a similarity metric minimum; and (3) halting the optimizing after either the iteration maximum equals about thirty or the similarity metric minimum falls below about $10^{-5}$.

In some embodiments, the step of applying a smoothing function comprises: (1) executing a B-spline transform wherein a deformation is defined by a grid of nodes superimposed on the first registration, the transform having a plurality of variables including node deformation; (2) selecting a similarity metric representing the alignment of the first registration to the first clinical image volume; and (3) optimizing the variables iteratively until the similarity metric achieves a minimum limit. In some embodiments, the step of executing a B-spline transform further comprises: (1) executing a first stage B-spline transform wherein the grid of nodes comprises a first grid of nodes arrayed at a first spacing distance superimposed on the first registration, the first stage producing an intermediate registration; and (2) executing a second stage B-spline transform wherein the grid of nodes further comprises a second grid of nodes arrayed at a second spacing distance superimposed on the intermediate registration, wherein the second spacing distance is shorter than the first spacing distance.

In some embodiments, the step of executing a voxelwise algorithm comprises: (1) executing a deformable image registration transform having a plurality of nonlinear variables; (2) defining at least a displacement vector at each voxel; (3) selecting a similarity metric representing the alignment of the smoother registration to the first clinical image volume; and (4) optimizing the nonlinear variables iteratively, according to the displacement vector, until the similarity metric achieves a minimum limit. In some embodiments, the step of optimizing further comprises optimizing the nonlinear variables according to a partial differential equation having a diffeomorphic update step. In some embodiments, the step of selecting further comprises selecting a similarity metric having a variational expression of a mutual information component that is varied according to a local value of an image intensity gradient based at least partially on the displacement vector.

According to further embodiments, the contents of a non-transitory computer-readable medium cause a computing system to perform a method of creating a synthetic computed-tomography (CT) image volume, wherein the method comprises: (1) obtaining a first clinical image volume; (2) retrieving a reference CT image volume; (3) applying a rigid registration algorithm to register the reference CT image volume to the first clinical image volume and thereby produce a first registration; (4) applying a smoothing function to the first registration and thereby produce a smoothed registration; and (5) applying a voxelwise intensity algorithm to the smoothed registration and thereby produce a synthetic CT image volume having characteristics correlated to those of the first clinical image volume. In some embodiments, method further comprises: (6) obtaining a second clinical image volume; (7) deriving a map of attenuation coefficients based on the synthetic CT image volume; and (8) correcting the second clinical image volume for attenuation based on the map.

In some embodiments, the step of applying a rigid registration algorithm comprises: (1) executing an affine transform algorithm having a plurality of variables including translation, rotation, scale, and shear; (2) selecting a similarity metric representing the alignment of the reference CT image volume to the first clinical image volume; and (3) optimizing the variables iteratively until the similarity metric achieves a minimum limit.

In some embodiments, the step of applying a smoothing function comprises: (1) executing a B-spline transform wherein a deformation is defined by a grid of nodes superimposed on the first registration, the transform having a plurality of variables including node deformation; (2) selecting a similarity metric representing the alignment of the first registration to the first clinical image volume; and (3) optimizing the variables iteratively until the similarity metric achieves a minimum limit.

In some embodiments, the step of executing a voxelwise algorithm comprises: (1) executing a deformable image registration transform having a plurality of nonlinear variables; (2) defining at least a displacement vector at each voxel; (3) selecting a similarity metric representing the alignment of the smoother registration to the first clinical image volume; and (4) optimizing the nonlinear variables iteratively, according to the displacement vector, until the similarity metric achieves a minimum limit.

BRIEF DESCRIPTION OF THE DRAWINGS

Figure 1:
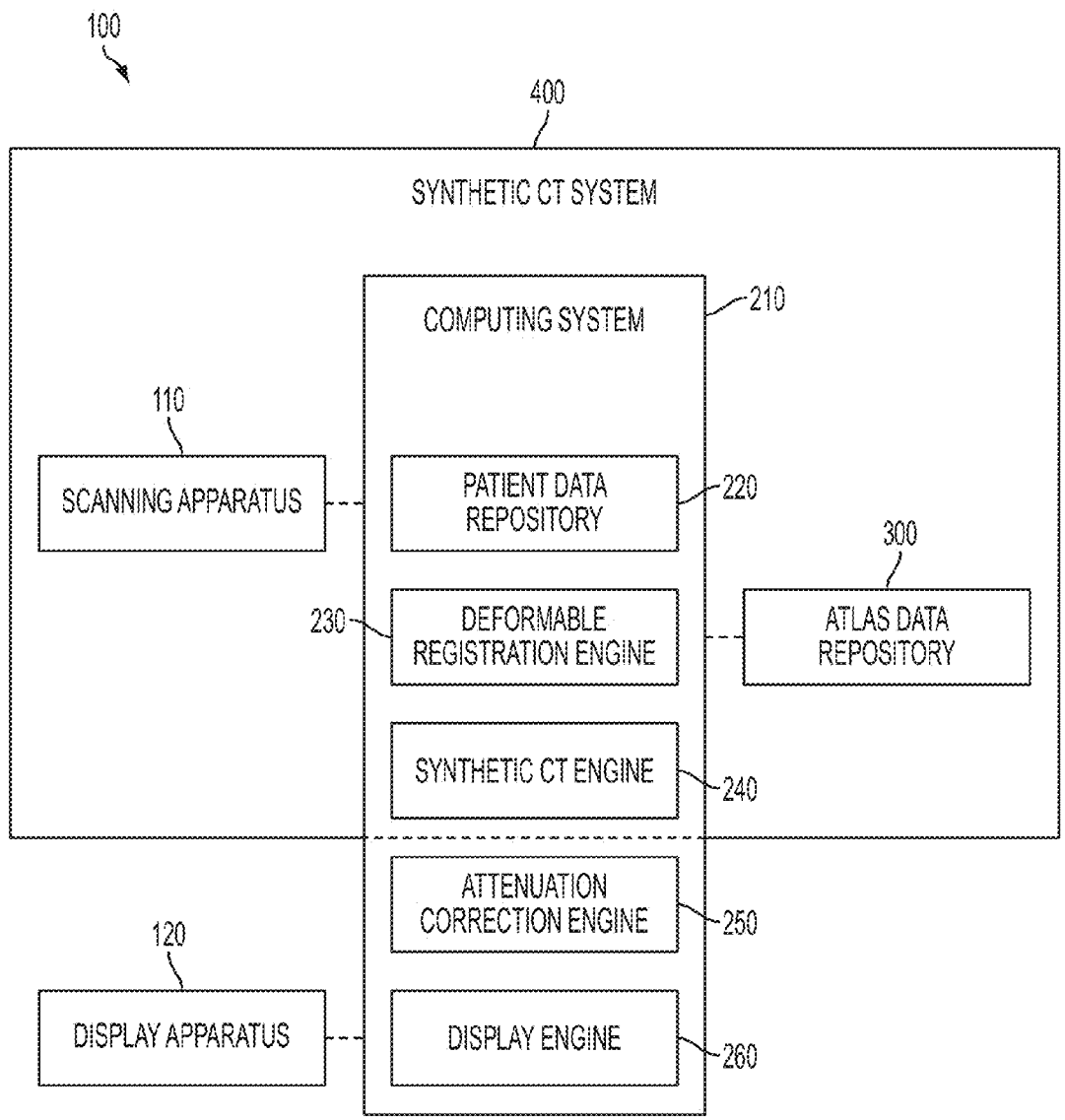

Having thus described various embodiments in general terms, reference will now be made to the accompanying drawings, which are not necessarily drawn to scale, and wherein:

FIG. 1 is a schematic illustrating an attenuation correction system, according to various embodiments.

Figure 2:
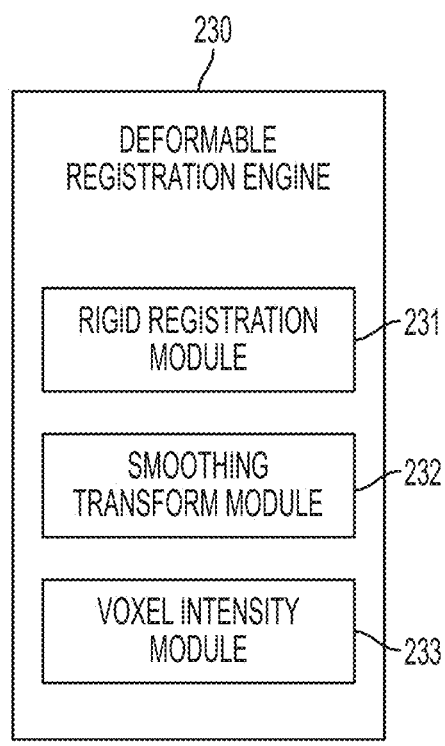

FIG. 2 is a schematic illustration of various embodiments of a registration engine.

Figure 3:
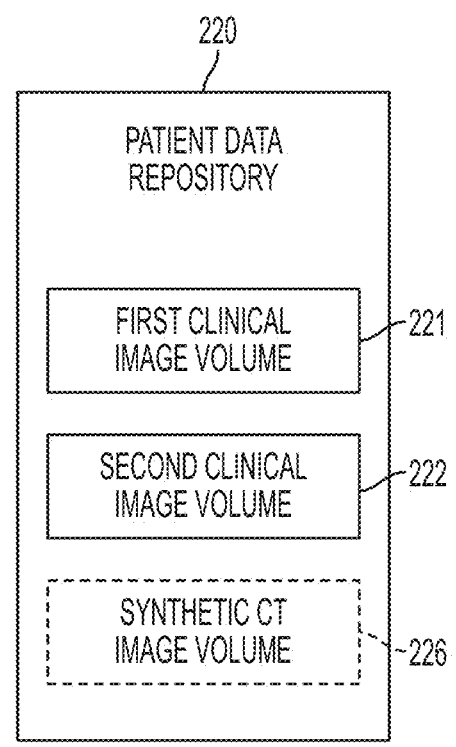

FIG. 3 is a schematic illustration of various embodiments of a patient data repository.

Figure 4:
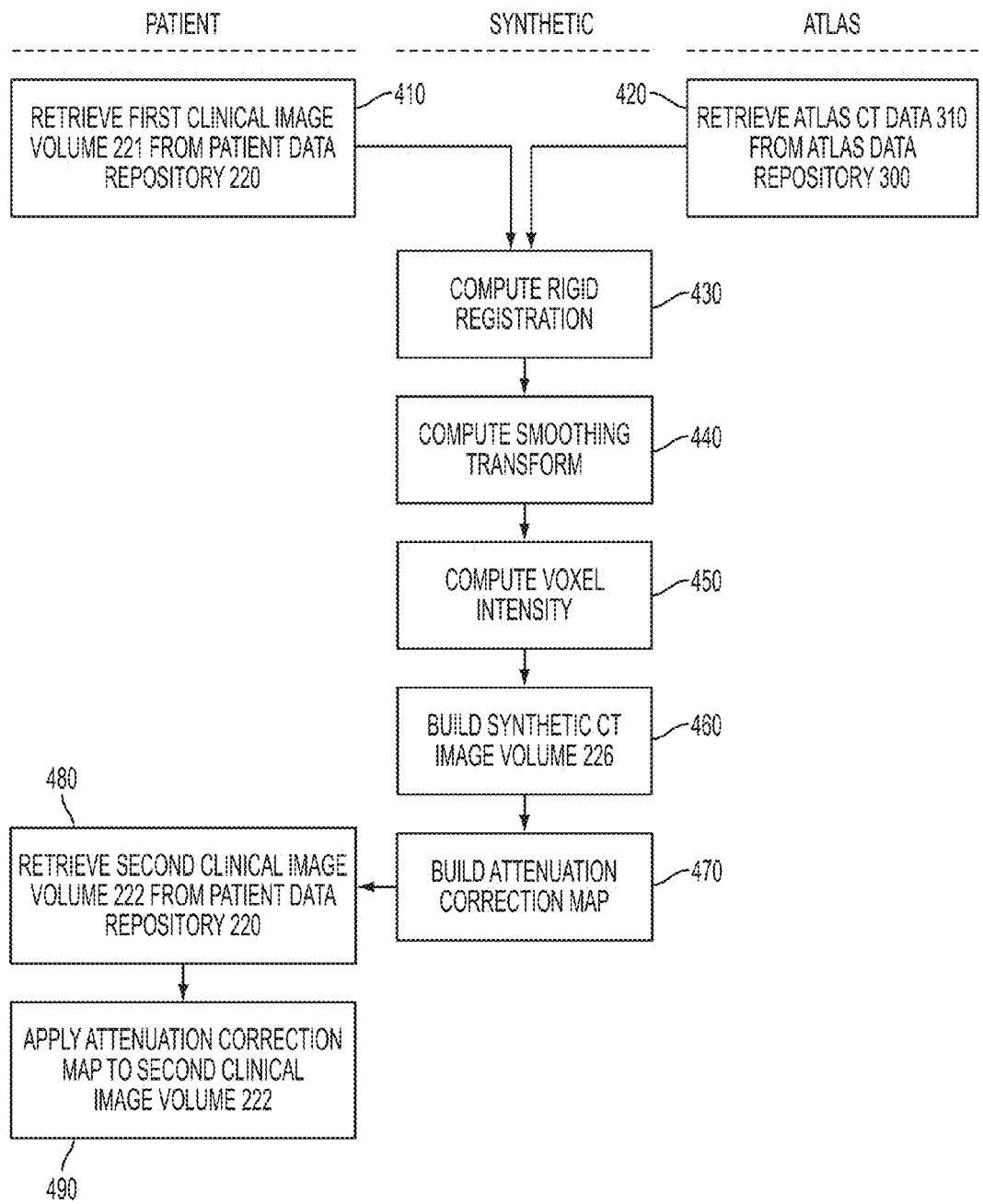

FIG. 4 is a flow chart illustrating a method of building and applying an attenuation correction map, according to various embodiments.

Figure 5:
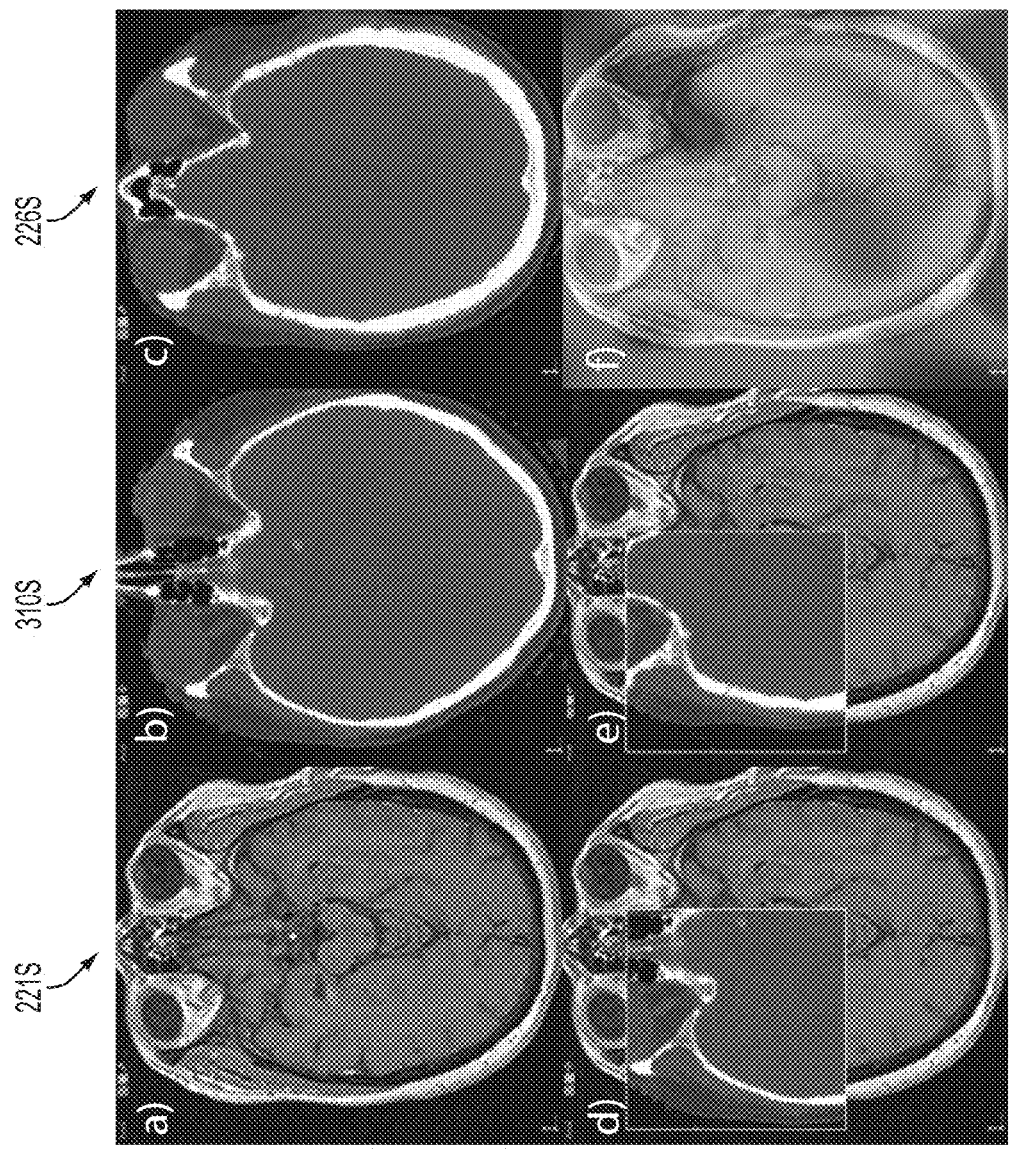

FIG. 5 is a series of images illustrating the typical results achieved by the deformable registration algorithms, according to various embodiments.

Figure 6:
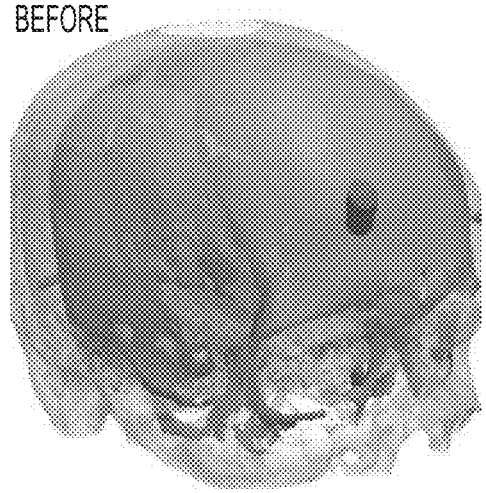
Figure 6:
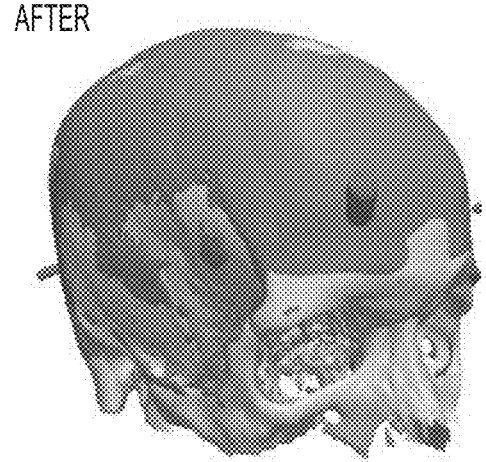
Figure 6:
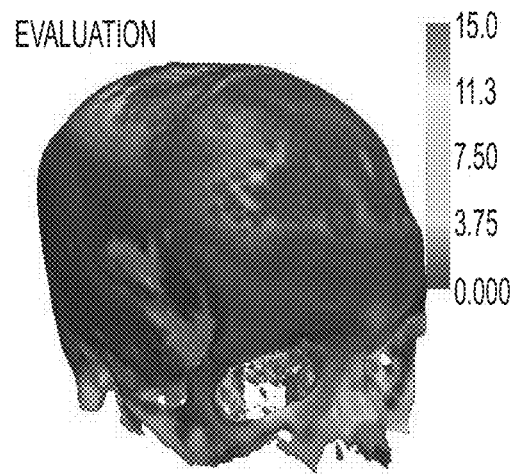

FIG. 6 is a series of three-dimensional surface images, illustrating a geometrical evaluation of the performance of the deformable registration algorithms, according to various embodiments.

Figure 7:
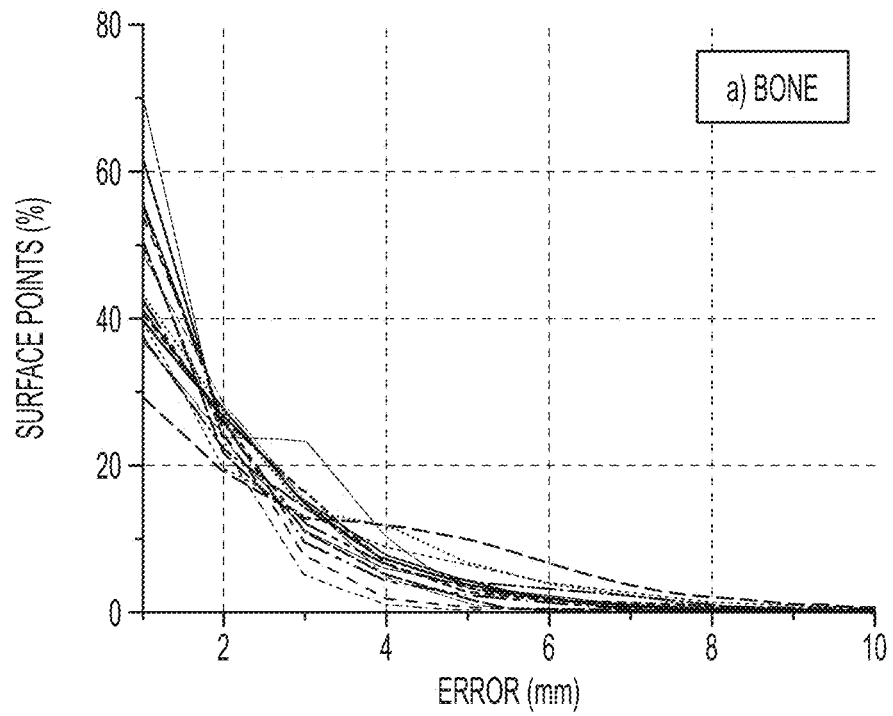
Figure 7:
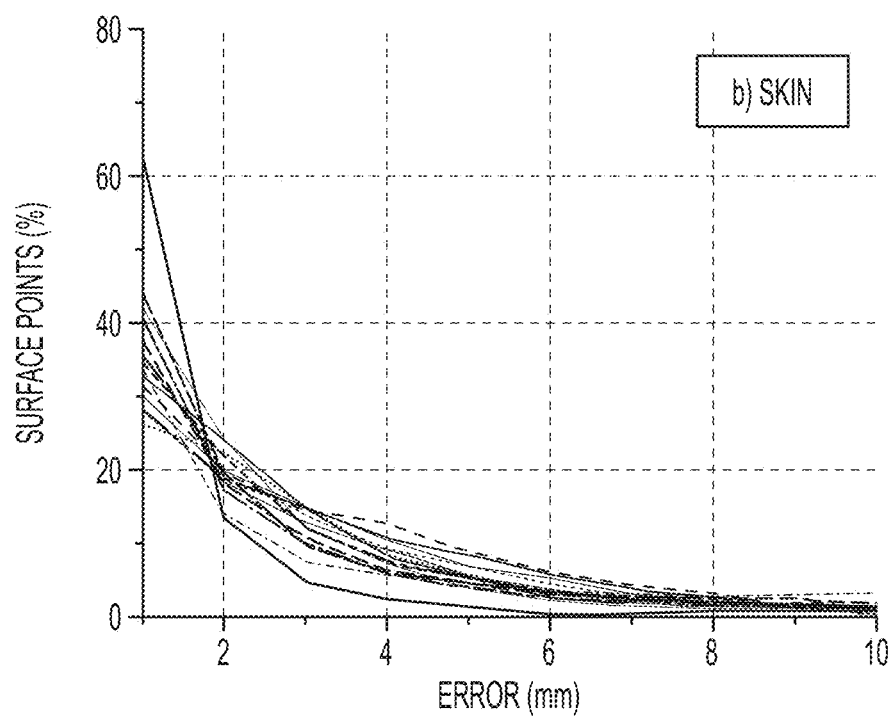

FIG. 7 is a series of histograms illustrating the typical results achieved by the deformable registration algorithms, according to various embodiments, in terms of geometric accuracy.

Figure 8:
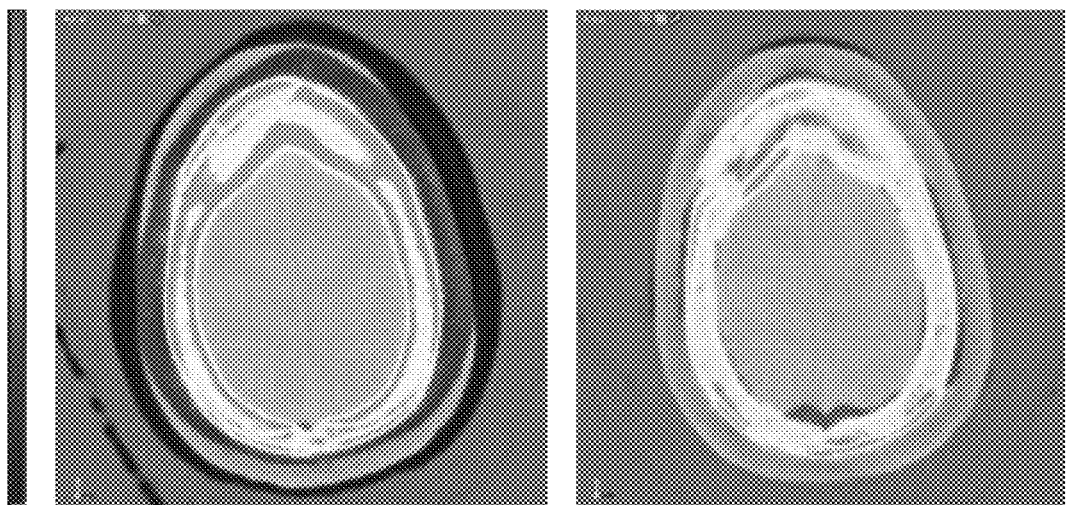

FIG. 8 is a series of tomographic images illustrating the typical results achieved by the deformable registration algorithms, according to various embodiments, in terms of voxelwise accuracy.

Figure 9:
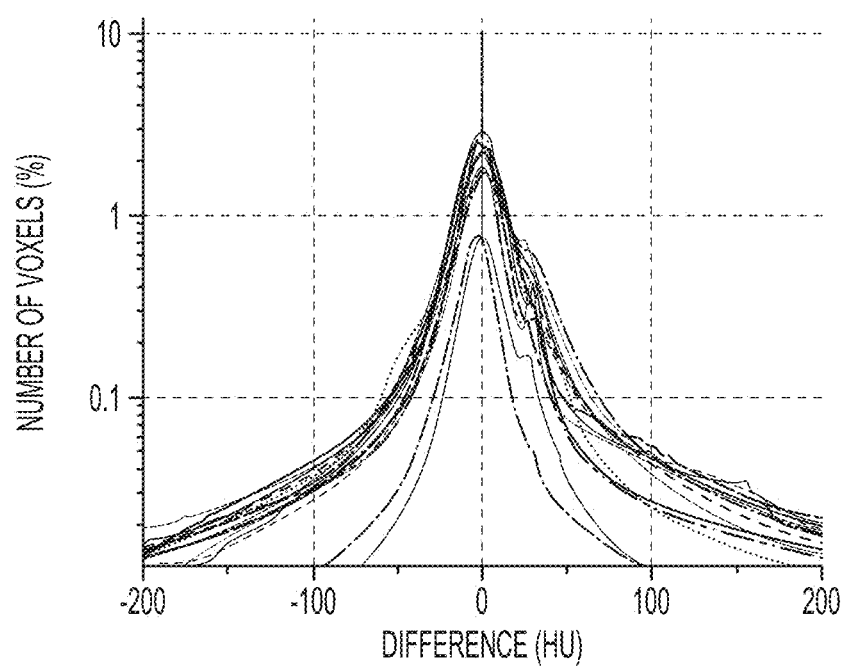

FIG. 9 is a histogram illustrating the typical results achieved by the deformable registration algorithms, according to various embodiments, in terms of voxelwise accuracy.

Figure 10:
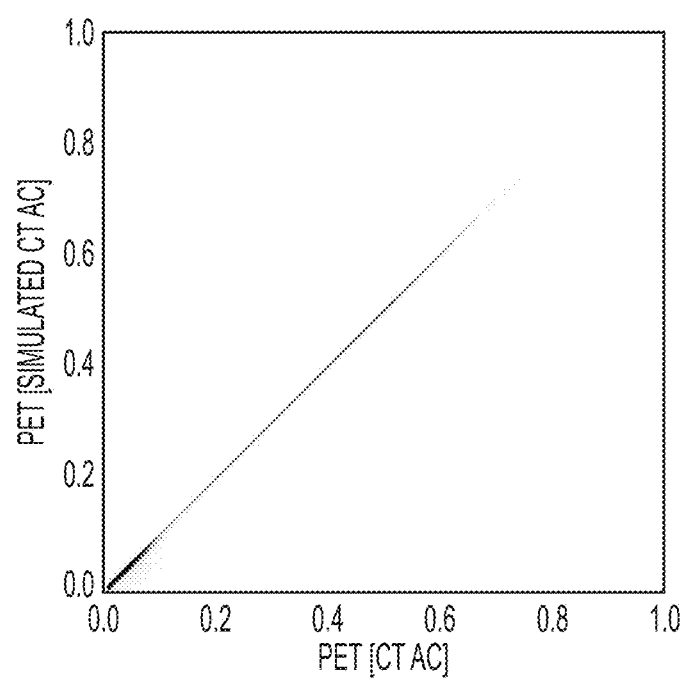

FIG. 10 is a histogram illustrating the typical results achieved by the deformable registration algorithms, according to various embodiments.

DETAILED DESCRIPTION OF VARIOUS EMBODIMENTS

Various embodiments of the present invention will now be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Various embodiments are directed toward systems for and methods of creating a synthetic computed tomography (CT) image. In some embodiments, the method of creating a synthetic CT image may begin obtaining a clinical dataset (sometimes called an "image volume") and selecting a reference CT image volume from a database or atlas of stored images. The clinical image volume may be obtained from a Magnetic Resonance (MR) scan, or from the MR data portion of a combination PET-MR or SPECT-MR scan, for example. SPECT stands for single-photon emission tomography. The method may include applying a series of rigid and deformable image registration techniques to correlate or match the reference CT image volume to the clinical image volume. In this aspect, the reference CT may be distorted or warped into substantially close correlation with the clinical image volume, thereby creating a synthetic CT image specific to the clinical subject or patient.

In some embodiments, the resulting synthetic CT image volume may be applied to a second clinical image volume, such as a PET data portion of a combination PET-MR or SPECT-MR scan, for example. A map of attenuation coefficients may be derived from the synthetic CT image volume. The map, in turn, may be applied to correct the attenuation present in the second clinical image volume. In this aspect, the synthetic CT may be used to correct the attenuation in a clinical image.

Although several embodiments are discussed with reference to a combined PET-MR scan of the head and brain, the invention may be applied to any of a variety of other scan modalities.

Exemplary Synthetic CT System 400

FIG. 1 illustrates various embodiments of a Synthetic CT System 400. The Synthetic CT System 400 typically comprises a Patient Data Repository 220, an Atlas Data Repository 300, a Deformable Registration Engine 230, and a Synthetic CT Engine 240. The Synthetic CT System 400 optionally comprises a Scanning Apparatus 110, a Computing System 210, and a Display Apparatus 120. In some embodiments, the Synthetic CT System 400 may be part of an Attenuation Correction System 100. Each of the elements in FIG. 1 may be embodied in hardware, software or computing instructions.

The Patient Data Repository 220, in some embodiments, may be configured to store raw image data obtained from the Scanning Apparatus 110 or from other sources, and may include other images, computing instructions, and other associated parameters such as image types, regions, weights, values and characteristics. The Patient Data Repository 220 may include static memory, magnetic memory, random access memory, non-volatile memory, volatile memory, magnetic storage, optical storage, and the like. The Patient Data Repository 220 is optionally configured to communicate with the Scanning Apparatus 110 through a direct connection, over a computing network, or through an alternative communication network. FIG. 3 illustrates various embodiments of a Patient Data Repository 220 which, as shown, comprises a patient-specific First Clinical Image Volume 221 and a Second Clinical Image Volume 222. In one embodiment, the First Clinical Image Volume 221 comprises an MR scan or the MR component of a combination PET-MR or a SPECT-MR scan. In one embodiment, the Second Clinical Image Volume 222 comprises a PET scan or the PET component of a PET-MR scan or a SPECT-MR scan. The Patient Data Repository 220 optionally comprises Synthetic CT Image Volume 226, generated in some embodiments by the Synthetic CT Engine 240.

The Scanning Apparatus 110 may comprise a medical imaging device using any of a variety of modalities, such as X-ray, Computed Tomography (CT), Magnetic Resonance (MR), Positron Emission Tomography (PET), and/or combined modalities such as PET-CT, SPECT-CT, PET-MR, SPECT-MR, and the like. The Display Apparatus 120 may comprise, for example, a television, computer monitor, liquid crystal display panel, LED panel, plasma display panel, CRT display, and the like. Both the Scanning Apparatus 110 and the Display Apparatus 120 are optionally configured to communicate with the Computing System 210 through a direct connection, over a computing network, or through an alternative communication network.

The Computing System 210 may comprise, for example, a personal computer, workstation, server, computing devices distributed over a network, and the like. The Computing System 210 comprises logic configured for performing computations and/or data processing associated with one or more modules or engines, as shown. For the Synthetic CT System 400, in some embodiments, this logic includes the Patient Data Repository 220, a Deformable Registration Engine 230, and a Synthetic CT Engine 240. For the Attenuation Correction System 100, in some embodiments, this logic may further include an Attenuation Correction Engine 250 and a Display Engine 260.

The Deformable Registration Engine 230, in some embodiments, may be configured to apply one or more rigid or deformable image registration algorithms to a reference CT image volume in order to register it with a patient-specific clinical image volume. The reference CT image volume may be obtained from any of a number of available image datasets, including patient data, clinical studies and atlas data. FIG. 2 illustrates various embodiments of a Deformable Registration Engine 230 which, as described below, may comprise a Rigid Registration Module 231, a Smoothing Module 232, and a Voxelwise Intensity Module 233.

The Synthetic CT Engine 240 may be configured in some embodiments to generate a synthetic CT image volume based on the results obtained by the Deformable Registration Engine 230. In some embodiments, the results obtained by the Deformable Registration Engine 230 include substantially all the characteristics of a synthetic CT image, in the same coordinate space, requiring no additional registration or adjustment.

The Atlas Data Repository 300, in some embodiments, may be configured to store raw image data from a reference atlas, reference images, deformable images, computing instructions, and other associated parameters such as image types, regions, weights, values and characteristics. The Atlas Data Repository 300 may include static memory, magnetic memory, random access memory, non-volatile memory, volatile memory, magnetic storage, optical storage, and the like. The Atlas Data Repository 300 is optionally configured to communicate with the Computing System 210 through a direct connection, over a computing network, or through an alternative communication network.

Atlas data is available from a variety of sources, and for a variety of anatomical regions. A brain atlas, for example, is a volume of reference images in which structures of interest have been carefully segmented, usually by hand. For example, Jean Talairach, a French neurosurgeon, created an atlas of postmortem sections of the brain of a sixty-year-old female subject. The Talairach brain atlas is used in medical image analysis, neurosurgery, and brain mapping. The Surgical Planning Laboratory (SPL) of the Harvard Medical School maintains an atlas dataset of CT images of normal brains. The University of California maintains an interactive brain atlas called BrainMaps, launched in 2005, that includes millions of scanned images of both primate and non-primate brains. The images are stored in a database that is available to physicians, medical imaging professionals, and the general public. The complete brain atlas dataset for the brain of a particular subject may include images of all the sections, as well as the raw data collected from a particular scan that was used to collect the images.

As a non-limiting example, a reference image volume called Atlas CT Data 310 may be stored in or accessed via the Atlas Data Repository 300 in some embodiments. The Atlas CT Data 310 may include a volume or series of images obtained by Computed Tomography (CT). A typical CT image may be comprised of an array of pixels; for example, 512 by 512 pixels. A pixel is a discrete two-dimensional unit that, together with others in the field of view, constitutes an image. Each pixel in a CT image may be displayed according to the mean attenuation of the corresponding tissue through which the X-ray passed. Attenuation refers to the gradual loss of X-ray energy that occurs as the X-rays pass through different tissues and structures in the body during a CT scan. The CT image, therefore, can provide a pixelwise (pixel-by-pixel) map of the corresponding attenuation values. The Hounsfield scale of attenuation may be used a reference, with +3071 being the most attenuating tissue and −1024 the least attenuating. Water has an attenuation of zero Hounsfield Units (HU); air is about −1000 HU; muscle is about +40 HU; bone ranges from +400 to +1000 HU and higher. Each pixel in a CT image may be described in terms of its HU value; each HU value may be correlated directly to a corresponding attenuation coefficient.

Deformable Registration Engine 230

The Deformable Registration Engine 230, in some embodiments, comprises a Rigid Registration Module 231, a Smoothing Module 232, and a Voxelwise Intensity Module 233. When the thickness of a tomographic image like a CT image is considered, the resulting three-dimensional unit is known as a volumetric pixel or a voxel. Voxelwise refers or relates to substantially each voxel in a three-dimensional image, voxel by voxel.

Image registration is the process of aligning different sets of data (image volumes, for example) into a common coordinate system. In the field of image processing, registration is typically described in terms of aligning a moving image onto a fixed image.

In mathematical terms, a registration procedure is an optimization process that recovers or finds the unknown variables (called transform parameters) by minimizing the differences between the two images as measured by a similarity metric (sometimes called a cost function). The transform parameters are the variables to be optimized. A transform (or transform function) is a mathematical expression, including a number of transform parameters, that describes the transformation or mapping between the moving image and the fixed image. The transform function maps the points in the moving image to homologous points in the fixed image. For example, if the moving image is located N units of distance away from the fixed image, along the x axis, then the transform function would be a mathematical formula reflecting a simple translation of all the points a distance of N units along the x axis. Of course, the transform function can be significantly more complex, especially in three dimensions (or four, including a time element), as the differences between the two images are greater.

A similarity metric may be used to measure how closely the two images are aligned during the optimization process. The metric may be expressed in terms of spatial similarity (by anatomical feature, for example) or in terms of voxel intensity similarity. During the optimization process, the similarity metric may be used to evaluate the relative value of the alignment between the two images for the current set of transform parameters.

The optimization process advances toward a solution by making iterative changes in the transform parameters. The alignment quality may be evaluated by the similarity metric after each iteration. Incremental variations to the transform parameters are continued as long as the similarity metric decreases (indicating progress toward a closer alignment), and may be discontinued or reversed if the similarity metric increases (indicating regression away from alignment).

The Deformable Registration Engine 230 in some embodiments comprises a series of registration procedures, each having its own transform function, optimizer function, and similarity metric. Also, each registration procedure may have its own set of initial parameter values, incremental iteration values, similarity metric constraints, and iteration constraints. Each of these modules may be embodied in hardware, software or computing instructions within the Computing System 210. Each of these modules may include one or more separate functions, routines, subroutines, algorithms or techniques. Compared to application of these modules or other routines separately, the application of these modules together may improve the speed of the mathematical convergence by the Deformable Registration Engine 230 toward a solution. Operation of the Deformable Registration Engine 230 in some embodiments may result in substantially a voxel-by-voxel correlation between the moving image and the fixed image.

In some embodiments, as illustrated in FIG. 2, the registration procedure begins with (1) a Rigid Registration Module 231 to obtain a rough or first registration; (2) continues with a Smoothing Module 232 to produce a smoothed registration; and (3) further refines the smoothed registration with a Voxelwise Intensity Module 233, in order to produce a moving image that may be substantially co-registered with the fixed image. In some embodiments where the moving image comprises Atlas CT Data 310 and the fixed image comprises a patient's First Clinical Image Volume 221, the Voxelwise Intensity Module 233 may produce a co-registered moving image that may be substantially equivalent to a patient-specific synthetic CT image because it is substantially correlated to the patient's own first clinical image.

Rigid Registration Module 231

The Rigid Registration Module 231 may be configured in some embodiments to begin the registration procedure by geometrically correlating a reference CT image volume (referred to as Atlas CT Data 310 in FIG. 4) to a First Clinical Image Volume 221. The Rigid Registration Module 23 in some embodiments may also be configured to select a suitable reference CT image from among a plurality of candidate CT images based on a similarity metric.

In some embodiments, the Rigid Registration Module 231 comprises a rigid, voxel-by-voxel registration process. In this aspect, the Rigid Registration Module 231 operates directly with the image intensity value at each voxel (in other words, the gray value at each voxel), thereby matching the anatomy visible in both images. Registration based on image intensity value produces closer anatomical alignment, as opposed to a simple spatial alignment. The similarity metric for the Rigid Registration Module 231 in some embodiments directly compares the image intensity value between the two images, voxel by voxel. This metric may work well for comparing image intensity values between two images obtained by the same modality; for example, comparing a first CT to a second CT. For multiple-modality image registration, however, the Rigid Registration Module 231 in some embodiments includes a more sophisticated and customized formulation because the intensity values are different for different modalities. For example, bone is relatively bright in CT but dark in MR imaging, while air is dark in both CT and MR images. The Rigid Registration Module 231 in some embodiments uses a similarity metric that includes a Mutual Information component.

The Mutual Information component expresses how much information in a first image is also contained in a second image. The closer the alignment; the higher the value of the Mutual Information component. The use of Mutual Information in medical image registration has been described by Mattes and others. See, for example, "PET-CT Image Registration in the Chest Using Free-form Deformations" by Mattes et al., in *IEEE Transactions on Medical Imaging*; January 2003; pages 120-128; Vol. 22, No. 1. The Mutual Information component in some contexts is based on an assumption that there exists a correlation between groups of voxels that have similar values. In this aspect, The Mutual Information component measures how much information one random variable (the image intensity value in one image, for example) tells about another random variable (image intensity in the other image).

In mathematical terms, the Rigid Registration Module 231 in some embodiments compares the image intensity values in the two images, voxel by voxel, using a voxel intensity histogram with a Mutual Information component. For two images, the Mutual Information component may be computed from the joint probability distribution, which is a function of the intensity values at each voxel in both images. When the images are aligned, the joint probability distribution is high, resulting in a sharp peak on the voxel intensity histogram, which indicates a high Mutual Information component.

The Rigid Registration Module 231 in some embodiments includes an automated similarity metric with a Mutual Information component that searches for a transform function between the moving image and the fixed image at which identical anatomical landmarks in both images are most closely overlapping. Any of a variety of rigid registration algorithms may be employed. In one embodiment, the Rigid Registration Module 231 uses the Mattes formulation of the Mutual Information metric (discussed below), with twenty-five bins and 5% samples of the total number of voxels used to build the statistics. The initial images are sub-sampled by two, to increase computational speed. A typical rigid registration may be obtained in about twenty seconds on a desktop computer. The transform function used by the Rigid Registration Module 231 in some embodiments comprises an affine transform function with variables in translation, rotation, scale and/or shear. One or more affine transform routines can be found in the Insight Tool Kit (ITK). The ITK is a library of image registration tools maintained in an open-source software library. In one embodiment, the transform function used by the Rigid Registration Module 231 is the AffineTransform function from the ITK library.

The Rigid Registration Module 231 in some embodiments may also include a general optimizer that seeks the global maximum of the similarity metric by iteratively modifying the parameters according to an optimization scheme. The similarity metric that includes a Mutual Information component, in some embodiments, may be used to compare the voxelwise image intensity values in the fixed image (denoted as I-fixed (i, j, k)), with the image intensity values in the moving image (I-moving (i, j, k)), where the coordinates (i, j, k) define the position of a voxel. In one embodiment, the similarity metric used by the Rigid Registration Module 231 is the MattesMutualInformationImageToImageMetric function from the ITK library. The optimizer's task is to find the global maximum of the similarity metric. In one embodiment, the optimizer used by the Rigid Registration Module 231 is the RegularStepGradientDescentOptimizer function from the ITK library. In one embodiment, the Rigid Registration Module 231 may also use a linear interpolator, such as the LinearInterpolatorImageFunction tool from the ITK library.

In some embodiments, the Rigid Registration Module 231 may include a set of stopping conditions based on a set of constraints, such as a maximum number of iterations or a minimum change in the similarity metric. The Rigid Registration Module 231 in some embodiments is configured to halt the process after either an iteration maximum equals thirty iterations or a similarity metric minimum change falls below $10^{-5}$. The maximum and minimum step sizes for the optimizer, in one embodiment, are 4 and $10^{-4}$, respectively.

In some embodiments, the Rigid Registration Module 231 produces a first registration between the two images. This first registration may undergo further refinement. In some embodiments, rigid registration alone may not achieve a sufficient registration. The first registration may represent a rough anatomical match between the reference CT image (the Atlas CT Data 310) and the First Clinical Image Volume 221.

Smoothing Module 232

The Smoothing Module 232 may be configured in some embodiments to apply a smoothing function to the first registration, in order to produce a smoothed registration. Whereas the Rigid Registration Module 231 in some embodiments included a rigid transform function with variables in several degrees of freedom (translation, rotation and scale, for example), the Smoothing Module 232 in some embodiments may include a deformable transform function with variables in many more degrees of freedom. The Smoothing Module 232 in some embodiments evaluates the transformation of each voxel independently, rather than viewing the whole image volume as a block. As in rigid registration, the Smoothing Module 232 in some embodiments evaluates the alignment between the moving image and the fixed image using a similarity metric and an optimizer.

In some embodiments the Smoothing Module 232 includes a B-spline transform function, where the deformation may be defined by a three-dimensional grid of nodes superimposed on the moving image (in this case, on the first registration of the moving image obtained during execution of the Rigid Registration Module 231, described above). In this aspect, the deformation of any particular node to another location may be obtained or calculated using B-spline interpolation. In this embodiment, the B-spline transform and grid keeps the number of variables to be optimized at a reasonable number, while the B-spline interpolation provides the flexibility to define small local deformations. One or more transform routines can be found in the Insight Tool Kit (ITK). In one embodiment, the B-spline transform function used by the Smoothing Module 232 is the BSplineTransform function from the ITK library.

While rigid registration may be a linear method, the B-spline transform accommodates multiple parameters and provides a flexible, nonlinear transformation. In the B-spline technique, generally, deformations of the object volume are achieved by tuning an underlying mesh or grid of spline points called nodes. The B-spline transform is categorized as a parametric function because using a finite number of parameters allows representation of non-rigid transformations with realistic complexity. In the B-spline approach, the deformation field is defined by a sparse lattice of nodes overlaid on the image and the displacement at any voxel is obtained by interpolation from the closest lattice nodes. In some embodiments, the number of B-spline nodes can be increased in a particular area of interest; a tactic that is significantly more successful if an equally spaced lattice of additional nodes is used.

In one embodiment, the B-spline transform of the Smoothing Module 232 uses the same settings for the Mutual Information metric as those used in the Rigid Registration Module 231. The optimizer in some embodiments may be changed to an implementation that is designed to better handle the large number of variables involved in the B-spline deformation model. One such optimizer is described by Liu and Nocedal in their paper, "On the Limited Memory BFGS Method for Large-Scale Optimization," published in *Mathematical Programming*, volume 45, pages 503-28, 1989. To increase speed and enhance the B-spline algorithm's ability to find the global minima, one embodiment employs a multi-resolution approach for the spline grid itself by successively increasing the number of nodes per dimension from five to ten and fifteen, at every fifty iterations of the optimizer. A typical B-spline transform may be obtained in about sixty seconds. This computation speed may be achieved, for example, by employing a multi-processor implementation of the Mattes metric in which different metric calculations are sent to one of four processors in a computational workstation. In some embodiments, the B-spline Transform Module 232 follows the theory presented by Mattes and colleagues in "PET-CT Image Registration in the Chest using Free-form Deformations," published in *IEEE Transactions on Medical Imaging*, volume 22, pages 120-28, 2003.

The optimizer function of the Smoothing Module 232, in some embodiments, iteratively modifies the node deformation until the similarity metric is maximized (indicating the differences between the moving image and the fixed image are minimized). The Smoothing Module 232 in some embodiments uses an optimizer that follows the Limited-memory Broyden Fletcher Goldfarb Shannon (LBFGS) minimization with simple bounds. The LBFGS minimizes a non-linear function of multiple variables, subject to simple boundary constraints. In one embodiment, the optimizer used by the Smoothing Module 232 is the LBFGSB function from the ITK library.

In some embodiments, the Smoothing Module 232 may include a set of initial conditions. For example, in some embodiments where the Smoothing Module 232 comprises a B-spline transform, the initial node spacing is set at five centimeters. The Smoothing Module 232 may also be configured to trim or crop the data in an image volume; for example, by selecting the surface of the skull plus five centimeters, in order to capture the entire anatomy including the external contour (skin). For the initial five-centimeter node spacing, the Smoothing Module 232 in some embodiments is configured to halt the process after either an iteration maximum equals thirty iterations or a similarity metric minimum change falls below $10^{-5}$. The maximum and minimum step sizes for the optimizer, in one embodiment, are 4 and $10^{-4}$, respectively.

In some embodiments, the Smoothing Module 232 comprises a B-spline transform with a second-stage node spacing set at 2.5 centimeters, to produce a finer registration. Starting with the results from the initial five-centimeter node spacing, the second-stage 2.5-centimeter nodes are optimized in some embodiments using the LBFGSB optimizer, with a termination condition set at fifty iterations per stage, or a decrease in similarity metric of less than $10^{-8}$, or a maximum number of five hundred corrections. In the optimizer, the bounds are set to limit the magnitude of the node deformations to less than ten centimeters on each axis.

In some embodiments, the Smoothing Module 232 produces a smoothed registration between the two images. At the end of the B-spline matching, the two images are often matched in shape and size, with occasional differences in detail such as small bony features or soft-tissue boundaries. In some embodiments, rigid registration followed by smoothing may not achieve a sufficient registration. The Smoothing Module 232 in some embodiments may be considered a "bulk" deformable registration. The smoothed registration may represent a closer anatomical and voxelwise match between the reference CT image (the Atlas CT Data 310) and the First Clinical Image Volume 221.

Voxelwise Intensity Module 233

The Voxelwise Intensity Module 233 may be configured in some embodiments to further refine the smoothed registration and thereby produce a moving image that is substantially co-registered with the fixed image. The Voxelwise Intensity Module 233 in some embodiments may be considered a "fine" deformable registration. The Voxelwise Intensity Module 233 may begin with an interpolated approximation obtained from the nodes of the B-spline function of the Smoothing Module 232 and further refine the registration by determining a voxelwise deformation field. In some embodiments where the moving image comprises Atlas CT Data 310 and the fixed image comprises a patient's First Clinical Image Volume 221, the Voxelwise Intensity Module 233 further refines the smoothed registration in order to create produce a co-registered moving image that is substantially equivalent to a patient-specific synthetic CT image. One aim of the Voxelwise Intensity Module 233 is to achieve a substantially voxel-by-voxel correspondence between the Atlas CT Data 310 and the First Clinical Image Volume 221.

In some embodiments, the Voxelwise Intensity Module 233 comprises a deformable registration algorithm that is designed to retain the advantages of optical flow algorithms, using an improved similarity metric capable of handling different image modalities, and using an improved update step capable of accommodating large inter-patient variations. Use of this deformable registration algorithm in the Voxelwise Intensity Module 233 incorporates both local information in the form of an image gradient and global information in the form of marginal and joint probability distributions of image signal intensities in the input images.

In some embodiments, the Voxelwise Intensity Module 233 comprises the application of an optical flow model, applied at each voxel separately, in order to define a displacement vector for each voxel. In this aspect, the Voxelwise Intensity Module 233 follows the voxel-by-voxel approach with a variational expression of the Mutual Information component as described by Hermosillo. In some embodiments, the similarity metric comprises the Mattes formulation of the Mutual Information metric, as described in "PET-CT Image Registration in the Chest Using Free-form Deformations" by Mattes et al., in *IEEE Transactions on Medical Imaging*; January 2003; pages 120-128; Vol. 22, No. 1. In some embodiments, the Mutual Information component is varied according to the local values of the image intensity gradient, as described by Hermosillo in "A Variational Approach to Multi-modal Image Matching," Technical Report 4117, INRIA, *Institut National de Recherche en Informatique et en Automatique*; February 2001. In some embodiments, the Voxelwise Intensity Module 233 may follow the Hermosillo approach as described by DeCraene and colleagues in, "Incorporating Metric Flows and Sparse Jacobian Transformations in ITK," The Insight Journal, http://hdl.handle.net/1926/183, March 2006. In some embodiments, the update step for the partial differential equation is diffeomorphic, in order to allow for large displacements, as described by Dupuis in "Variational Problems on Flows of Diffeomorphisms for Image Matching," *International Journal of Computer Vision*, Vol. 50, pages 329-343 (2002).

In some embodiments, the Voxelwise Intensity Module 233 comprises a gradient normalization scheme in accordance with the one described by Vemuri in "Image Registration via Level-set Motion: Applications to Atlas-base Segmentation," *Medical Image Analysis*, Vol. 7, pages 1-20 (2003). This gradient normalization, in some embodiments, is obtained from the magnitude of the motion vector—as a function of the differences in image intensity between the fixed and moving voxel—with an adaptive time step calculated by normalizing to the maximum motion vector over the entire field to ensure stability. With this normalization scheme, the update motion vectors are directly proportional to the gradients, scaled by the maximum gradient over the entire field.

This formulation of the deformable registration algorithm of the Voxelwise Intensity Module 233, in some embodiments, can be summarized as follows. (1) Estimate the vector flow, v, as described by Hermosillo in "A Variational Approach to Multi-modal Image Matching," Technical Report 4117, INRIA, *Institut National de Recherche en Informatique et en Automatique*; February 2001, and by Cuadra in "Dense Deformation Field Estimation for Atlas-based Segmentation of Pathological MR Brain Images," *Computer Methods and Programs in Biomedicine*; 2006; pages 66-75; Vol. 84. (2) Normalize the vector flow, v, across the dataset using the approach described by Vemuri in "Image Registration via Level-set Motion: Applications to Atlas-base Segmentation," *Medical Image Analysis*, Vol. 7, pages 1-20 (2003). (3) Compute an exponentiation, exp(v), of the field using the approach described by Vercauteren in "Non-parametric Diffeomorphic Image Registration With the Demons Algorithm;" *Medical Image Computing and Computer-Assisted Intervention;* 2007; pages 319-326; Vol. 10. (4) Add exp(v) to the current estimate of the displacement field. (5) Regularize the deformation field using a Gaussian smoothing.

In some embodiments, the constraints for the similarity metric in the Voxelwise Intensity Module 233 may be set at one hundred histogram bins and usage of all voxel intensity values in the input images. The displacement field may be smoothed at algorithm completion with a Gaussian kernel of width 2. In some embodiments, the Voxelwise Intensity Module 233 includes a termination condition set at fifty iterations.

Application of this multi-modality formulation in the Voxelwise Intensity Module 233 incorporates both local information in the form of image gradient and global information in the form of marginal and joint probability distributions of image signal intensities in the input images. A typical registration using the three modules of the Deformable Registration Engine 230, as described above, may be completed in about three minutes.

Method of Building a Synthetic CT Image Volume 226

FIG. 4 illustrates methods of building a synthetic CT image volume 226, as well as applying an attenuation correction map, according to various embodiments. Typically, these methods include the use of a First Clinical Image Volume 221 image and Atlas CT Data 310 to build a synthetic patient-specific CT image volume 226. As shown, the method steps are generally divided into columns representing the different sources of data: patient data, synthetic data, and atlas data. Although the examples illustrated in FIG. 4 depict the use of separate Compute and Build steps, these steps or functions may be accomplished in combination or separately, and in any order suitable to a particular application.

In some embodiments, the method of building a synthetic CT image may begin in Step 410 by selecting and retrieving a First Clinical Image Volume 221 from a Patient Data Repository 220. In one embodiment, the First Clinical Image Volume 221 comprises MR data from a patient scan. Step 420 includes selecting and retrieving the Atlas CT Data 310 from an Atlas Data Repository 300. The three computation steps 430, 440, 450 in the center column represent the three modules executed by the Deformable Registration Engine 230, as described above.

In one embodiment of Step 430, a rigid registration is computed using the algorithms and functions in the Rigid Registration Module 231. Rigid registration may be the first step in distorting or warping the Atlas CT Data 310 to the Second Clinical Image Volume 222 and, in some embodiments, may be accomplished using a linear function. The Compute Rigid Registration Step 430 in some embodiments applies one or more mathematical functions in order to distort or warp the Atlas CT Data 310 to more closely match the geometry of the Second Clinical Image Volume 222. The functions in some embodiments include rigid registration routines selected from the open-source ITK library. The functions in some embodiments include the use of the Mattes formulation of the Mutual Information metric, with twenty-five bins and 5% samples of the total number of voxels to build the statistics. In operation, the Compute Rigid Registration Step 430 may be repeated for a number of iterations until the resulting registration satisfies one or more limiting parameters. In some embodiments, different limiting parameters may be applied for different regions or portions of the image.

In one embodiment of Step 440, a B-spline transform function may be computed as part of the Smoothing Module 232. The Compute Smoothing Transform Step 440 in some embodiments begins with the results of the Compute Rigid Registration Step 430 and continues refining the registration. In some embodiments, the Compute Smoothing Transform Step 440 comprises the steps of setting multiple parameters, tuning an underlying lattice of spline points called nodes, overlaying on the image a lattice of nodes either sparsely or densely (depending on the degree of deformation in a region), and optimizing the variables to improve computing speed and accuracy. In operation, the Compute Smoothing Transform Step 440 may be repeated for a number of iterations until the resulting registration satisfies one or more limiting parameters. In some embodiments, different limiting parameters may be applied for different regions or portions of the image.

In one embodiment of Step 450, a voxel intensity deformation function may be computed using the Voxelwise Intensity Module 233. The Compute Voxel Intensity Step 450 in some embodiments begins with the results of the Compute Smoothing Transform Step 440 and continues refining the registration. More specifically, the Compute Voxel Intensity Step 450 may begin with an interpolated approximation obtained from the lattice of nodes applied in the Compute Smoothing Transform Step 440. In some embodiments, the Compute Voxel Intensity Step 450 comprises the application of an optical flow model and a similarity metric (such as the Mutual Information component, described above) for monitoring progress during multiple iterations. The optical flow model in some embodiments may be applied at each voxel separately, in order to define a displacement vector for each voxel. In this aspect, the Compute Voxel Intensity Step 450 may follow the voxel-by-voxel approach with a variational expression of the Mutual Information metric as described by Hermosillo in, "A Variational Approach to Multi-modal Image Matching," Technical Report 4117, INRIA, 2001. In operation, the Compute Voxel Intensity Step 450 may be repeated for a number of iterations until the resulting registration satisfies one or more limiting parameters. In some embodiments, different limiting parameters may be applied for different regions or portions of the image.

In some embodiments of Step 460, the results obtained by the three Compute steps 430, 440, 450 (described above) include substantially all the characteristics of a synthetic CT image, in the same coordinate space, requiring no additional registration or adjustment. In this aspect, the Build Synthetic CT Step 460 may comprise only handling, sending or storing the results of the three Compute steps 430, 440, 450 in the form of a standard CT image volume. In some embodiments, the Build Synthetic CT Step 460 may comprise collecting the data or building a Synthetic CT Image Volume 226 using the Synthetic CT Engine 240.

Method of Correcting Attenuation using a Synthetic CT Image

Beginning with Step 470, FIG. 4 illustrates methods of building and applying an attenuation correction map based on a synthetic CT image volume 226. Although the examples illustrated in FIG. 4 depict the use of separate Compute and Build steps, these steps or functions may be accomplished in combination or separately, and in any order suitable to a particular application.

In some embodiments of Step 470, a map of attenuation correction coefficients is built using the Synthetic CT Image Volume 226 and the Attenuation Correction Engine 250 (shown in FIG. 1). In one embodiment of Step 470, the Synthetic CT Image Volume 226 includes substantially all the characteristics of an attenuation correction map. Each pixel in a CT image may be described in terms of its HU value; each HU value may be correlated directly to a corresponding attenuation coefficient. Accordingly, the Build Synthetic CT Step 460 may comprise the pixelwise translation of HU values in the synthetic CT image to its corresponding attenuation coefficient, thereby producing an attenuation correction map.

In some embodiments, Step 480 comprises retrieving a Second Clinical Image Volume 222 from a Patient Data Repository 220. In one embodiment, the Second Clinical Image Volume 222 comprises the PET data component from a combination PET-MR scan.

Step 490, in some embodiments, comprises the applying of the attenuation correction coefficient map to the Second Clinical Image Volume 222 in order to adjust or correct the attenuation therein. For the embodiment wherein the Second Clinical Image Volume 222 comprises the PET data component from a combination PET-MR scan, the Step 490 comprises the step of using the attenuation correction map as a guide for correcting the attenuation of photon energy that occurs during a PET scan. In this aspect, the stored patient-specific PET data component can be corrected using the map in order to produce an accurate PET image with attenuation correction. Because the Synthetic CT Image Volume 226 was registered to the patient's own First Clinical Image Volume 221, the resulting attenuation correction map is also specific to the patient's own anatomy. In this aspect, applying the attenuation correction map in Step 490 produces a PET image that is specifically correlated and attenuation-corrected to match the patient.

Exemplary Attenuation Correction System 100

Referring again to FIG. 1, it illustrates various embodiments of an Attenuation Correction System 100 that typically comprises some or all of the Synthetic CT System 400 as described above including a Scanning Apparatus 110, a Computing System 210, an Atlas Data Repository 300 and optionally a Display Apparatus 120. Each of the elements in FIG. 1 may be embodied in hardware, software or computing instructions.

The Attenuation Correction System 100 in some embodiments may be configured to include, optionally as part of a Computing System 210, an Attenuation Correction Engine 250 and a Display Engine 260 in communication with a Display Apparatus 120.

The Attenuation Correction Engine 250 may be configured to generate an attenuation correction map. In some embodiments, the Attenuation Correction Engine 250 may build a map of attenuation correction coefficients capable of altering or correcting the attenuation present in image data gathered from any of a variety of sources.

The Display Engine 260 may be configured to prepare image data for display on a Display Apparatus 120. The Display Engine 260 is optionally configured to communicate with the Display Apparatus 120 through a direct connection, over a computing network, or through an alternative communication network.

Evaluation of Results

For the evaluation process, one representative patient was selected from among the seventeen cases to serve as the Atlas CT Data 310. This atlas CT dataset was mapped sequentially to each set of patient MR data, resulting in a synthetic CT that matched the patient's anatomy. Additionally, each patient's CT imaging study (referred to as the acquired CT) was rigidly registered to its MR dataset. These evaluation steps were done in order to compare the synthetic CT to the acquired CT in terms of both geometrical accuracy and voxel intensity.

To evaluate the accuracy of the attenuation correction, seventeen clinical brain tumor cases were randomly selected and studied using acquired MR-CT images obtained less than one day apart. The Synthetic CT Image Volume 226 was compared to the patient's true CT in order to assess the geometrical accuracy of the Deformable Registration Engine 230 as well as to conduct voxel-by-voxel comparison, measured in Hounsfield Units (HU). In all cases, mapping from the Atlas CT Data 310 to the patient's Second Clinical Image Volume 222 was achieved with geometrical accuracy as judged using quantitative inspection tools. The mean distance between points in the Synthetic CT Image Volume 226 and the true CT external contour and bony anatomy was 1.26 and 2.15 mm, respectively. In terms of HU comparison, the mean voxel-to-voxel difference was less than 2 HU for all cases.

Evaluation of Synthetic CT Images

Typical results achieved by the Deformable Registration Engine 230, in some embodiments, on a sample patient dataset are illustrated in FIG. 5. An axial slice through a Sample First Clinical Image Volume 221S (in this case, an acquired MR dataset) is illustrated in inset (a). The corresponding slice from a Sample Atlas CT Dataset 310S (before registration) is illustrated in inset (b). There are evident differences between the two images. Inset (c) illustrates a Sample Synthetic CT Image Volume 226S, obtained by an exemplar application of the Deformable Registration Engine 230. As shown, the Deformable Registration Engine 230 substantially corrected the differences previously observable between the two images.

The accuracy of the Deformable Registration Engine 230 is further illustrated by overlaying a selections portions of insets (b) and (c) onto the MR dataset shown in inset (a). Inset (d) illustrates a portion of the Sample Atlas CT Dataset 310S (before registration) overlaid onto the MR dataset. Inset (e) illustrates a portion of the Sample Synthetic CT Image Volume 226S (after registration) overlaid onto the MR dataset. The anatomical features in the MR dataset and the Sample Synthetic CT Image Volume 226S are highly similar, as illustrated in FIG. 5(e).

The deformation field is illustrated in inset (f). The regions where large deformations existed are shown in lighter gray. These regions correspond closely with the regions that required the most warping or adjustment by the Deformable Registration Engine 230.

For a quantitative geometrical evaluation of registration results produced by the Deformable Registration Engine 230, a surface comparison tool was developed. The results are presented in FIG. 6. For the surface comparison, a surface was first selected that could be automatically delineated to eliminate subjectivity. The skull was selected and is illustrated in FIG. 6. This surface was extracted independently from the two datasets using a marching cube algorithm, which is a fully automated segmentation algorithm in which the HU value is the only parameter of the structure to be segmented. As illustrated in FIG. 6, in the "BEFORE" and "AFTER" illustrations, the skull surface extracted from the patient's true CT dataset is illustrated in dark gray. The skull surface extracted from the Atlas CT Data 310 is illustrated in lighter gray. To mathematically quantify geometrical errors in the registration, the Euclidean distances were computed between the two surfaces. Specifically, for every point in the skull surface extracted from the patient's true CT dataset, the distance to the closest cell of the corresponding skull surface extracted from the synthetic CT dataset was calculated. After calculation process, the surface was color-coded according to the results, as illustrated in the "EVALUATION" illustration of FIG. 6, with the darkest gray assigned to the minimum separation distance (near zero) and the lighter gray colors assigned to the maximum separation distance. A scale is provided near the "EVALUATION" illustration of FIG. 6. This evaluation method is superior to classical evaluation tools because many solutions exist to the registration problem, and these solutions are indiscernible with respect to the deformation inside a homogenous structure.

To analytically evaluate the geometry of the results produced by some embodiments the Deformable Registration Engine 230, the surface comparison tool was used to compare surfaces of bone and external contour (skin). Distances between the representative surface extracted from the Synthetic CT 226 and the acquired CT were quantitatively analyzed using histograms, as illustrated in FIG. 7. For the bony anatomy, FIG. 7(*a*), and skin contour, FIG. 7(*b*), a good match was observed. Only about 20% of the surfaces showed an error larger than two millimeters. For all cases, the percentage of error distances smaller than three millimeters for the bone surfaces ranged from 73.1% to 98.0%. The percentage of error distances smaller than five millimeters for the skin surfaces ranged from 77.8% to 89.2%. Errors larger than one centimeter appeared in less than 1% of the surface in all cases for bone surfaces and less than 2% for skin surfaces. The largest errors appeared in the sinus regions for the bony structures. The errors associated with the skin were produced by external devices that may not have been present in both datasets, or in different positions (for example, stereotactic head frames or therapy immobilization devices).

Voxelwise Evaluation of Synthetic CT Images

For evaluation of the voxel intensities, the global accuracy of the method was evaluated using an image difference tool. First, the Atlas CT Data 310 was registered to the patient's Second Clinical Image Volume 222 using the Deformable Registration Engine 230 described herein, to correct for anatomical changes. The acquired CT was also registered to the same Second Clinical Image Volume 222 using a rigid registration technique that included rotation and scaling. Because the two registrations for the synthetic and acquired CT are placed in the same frame of reference, a direct voxel-by-voxel difference of their HU values could be used to evaluate the algorithm's deviation from the intensities in the acquired CT. For a quantitative evaluation, histograms were used to graph the number of voxels versus HU differences for each patient (see FIG. 9).

A typical image difference between the two datasets is illustrated in FIG. 8; before execution of some embodiments of the Deformable Registration Engine 230 (on the left) and after (on the right). The differences, from −1000 HU to +1000 HU, are illustrated in gray scale, overlaid on the acquired CT scan. The scalar bar on the left shows the gray scale; the darker gray colors indicate larger differences. Before execution of some embodiments of the Deformable Registration Engine 230, large discrepancies existed because the datasets came from different patients. After execution of some embodiments of the Deformable Registration Engine 230, the differences were significantly reduced. Only relative small differences at the interfaces between the different tissue types were observed.

For a quantitative analysis of the results of some embodiments of the Deformable Registration Engine 230, several histograms of the differences were plotted and illustrated in FIG. 9. The histogram in FIG. 9 illustrated the number of voxels (expressed as a percentage) as a function of HU spatial difference or error (express in Hounsfield unites). A logarithmic scale was used for the y axis because, for most voxels, the differences were less than 1%. The histogram illustrated has been enlarged to show the region between −200 and +200 HU.

Evaluation of Attenuation Correction Using Synthetic CT Images

The use of synthetic CT data for attenuation correction of PET data was demonstrated with a fluorodeoxyglucose (FDG) PET brain study. A patient was injected with 555 megabecquerels (MBq) of FDG followed by a sixty-minute uptake period and then a ten-minute single-bed PET scan of the head on a PET/CT scanner. The associated CT imaging study was used to estimate the attenuation of the radiopharmaceutical distribution and PET attenuation correction factors. Data were reconstructed with an ordered-subset expectation maximization algorithm with random, scatter and attenuation corrections. An MR scan acquired on the same day was transformed to a synthetic CT using the Deformable Registration Engine 230 described herein. The Deformable Registration Engine 230 was also used for attenuation correction in a second reconstruction of the PET data. The two PET reconstructions were compared by plotting a normalized joint histogram. FIG. 10 shows the normalized joint histogram of PET image data using the original CT (along the x axis) compared to the PET image data with attenuation correction provided by the synthetic CT (y axis). Agreement between the two datasets was high, as illustrated by the narrow width of the histogram and its concentration along the line of unity.

CONCLUSION

Several embodiments and possible uses are specifically illustrated and/or described herein; however, the systems and methods described herein are equally applicable to image registration, synthetic image generation, and other applications outside the field of medical imaging. Terms used herein that relate or refer to human anatomy, for example, may be read to include structures other than human biology or morphology. Likewise, terms used herein that relate or refer to clinical data or images may be read to include data and image volumes other than those obtained in a clinical setting. In various embodiments, the systems and methods described herein may be configured to create a synthetic CT image volume that is based on an actual patient scan and conforms to the patient's anatomy, without necessarily subjecting the patient to an actual CT scan. The data in a synthetic CT image volume can be used for developing treatment protocols, surgical plans, and other medical services. In various embodiments, some or all of the modules described herein are stored in the form of computing instructions on a computer readable medium. The modules described herein may include hardware or software embodied in a non-transitory computer readable medium. The systems and methods described may be applied to two- or three-dimensional images, and may be applied in four-dimensional systems that include, for example, a time element.

Many modifications and other embodiments of the invention will come to mind to one skilled in the art to which this invention pertains having the benefit of the teachings presented in the foregoing descriptions and the associated drawings. For example, as will be understood by one skilled in the relevant field in light of this disclosure, the invention may take form in a variety of different mechanical and operational configurations. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computing system for creating a synthetic computed-tomography (CT) image volume, comprising:

processing circuitry comprising a processor and memory;

a rigid registration algorithm, which when implemented by the processing circuitry, is configured to register a reference CT image volume to a first clinical image volume and thereby produce a first registration;

a smoothing function, which when implemented by the processing circuitry, is configured to further refine said first registration and thereby produce a smoothed registration;

a voxelwise intensity algorithm, which when implemented by the processing circuitry, is configured to further refine said smoothed registration and thereby produce said synthetic CT image volume having characteristics correlated to those of said first clinical image volume;

an attenuation coefficient map generating algorithm, which when implemented by the processing circuitry, is configured to derive a map of attenuation coefficients based on said synthetic CT image volume; and an attenuation correction engine, which when implemented by the processing circuitry, is configured to correct attenuation in a second clinical image volume based on said map of attenuation coefficients.

2. A computing system for creating a synthetic computed-tomography (CT) image volume, comprising:

processing circuitry comprising a processor and memory;

a rigid registration algorithm, which when implemented by the processing circuitry, is configured to register a reference CT image volume to a first clinical image volume and thereby produce a first registration, wherein said rigid registration algorithm is further configured to register said first clinical image volume to each of a plurality of candidate CT image volumes and thereby obtain a plurality of corresponding candidate similarity metrics;

a smoothing function, which when implemented by the processing circuitry, is configured to further refine said first registration and thereby produce a smoothed registration;

a voxelwise intensity algorithm, which when implemented by the processing circuitry, is configured to further refine said smoothed registration and thereby produce said synthetic CT image volume having characteristics correlated to those of said first clinical image volume; and a selection tool, which when implemented by the processing circuitry, is configured to select said reference CT image volume from among said plurality of candidate CT image volumes based on a comparison of each of said plurality of corresponding candidate similarity metrics to a desired similarity metric.

3. The computing system of claim 1, wherein said rigid registration algorithm comprises:

an affine transform algorithm having a plurality of variables including translation, rotation, scale, and shear;

a similarity metric representing alignment of said reference CT image volume to said first clinical image volume;

an optimizer configured to iteratively adjust said plurality of variables until said similarity metric achieves a minimum limit.

4. The computing system of claim 3, wherein said optimizer further comprises:

an iteration maximum;

a similarity metric minimum; and a module configured to halt optimizing after either said iteration maximum equals about thirty or said similarity metric minimum falls below $10^{-5}$.

5. The computing system of claim 1, wherein said smoothing function comprises:

a B-spline transform wherein a deformation is defined by a grid of nodes superimposed on said first registration, said B-spline transform having a plurality of variables including node deformation;

a similarity metric representing alignment of said first registration to said first clinical image volume; and an optimizer configured to iteratively adjust said plurality of variables until said similarity metric achieves a minimum limit.

6. The computing system of claim 5, wherein said B-spline transform comprises:

a first stage B-spline transform wherein said grid of nodes comprises a first grid of nodes arrayed at a first spacing distance superimposed on said first registration, said first stage B-spline transform producing an intermediate registration; and a second stage B-spline transform wherein said grid of nodes further comprises a second grid of nodes arrayed at a second spacing distance superimposed on said intermediate registration, wherein said second spacing distance is shorter than said first spacing distance.

7. The computing system of claim 1, wherein said voxelwise intensity algorithm comprises:

a deformable image registration transform having a plurality of nonlinear variables;

a displacement vector defined at least at each voxel;

a similarity metric representing alignment of said smoothed registration to said first clinical image volume; and an optimizer configured to iteratively adjust said plurality of nonlinear variables according to said displacement vector until said similarity metric achieves a minimum limit.

8. The computing system of claim 7, wherein said optimizer is further configured to iteratively adjust said plurality of nonlinear variables according to a partial differential equation having a diffeomorphic update step.

9. The computing system of claim 7, wherein said similarity metric comprises a variational expression of a mutual information component that is varied according to a local value of an image intensity gradient based at least partially on said displacement vector.

10. A method of creating a synthetic computed-tomography (CT) image volume, comprising:

obtaining a first clinical image volume;

retrieving a reference CT image volume;

applying a rigid registration algorithm to register said reference CT image volume to said first clinical image volume and thereby produce a first registration;

applying a smoothing function to said first registration and thereby produce a smoothed registration;

applying a voxelwise intensity algorithm to said smoothed registration and thereby produce said synthetic CT image volume having characteristics correlated to those of said first clinical image volume;

obtaining a second clinical image volume;

deriving a map of attenuation coefficients based on said synthetic CT image volume; and correcting said second clinical image volume for attenuation based on said map of attenuation coefficients.

11. The method of claim 10, wherein said step of retrieving said reference CT image volume comprises:

establishing a desired similarity metric;

selecting a plurality of candidate CT image volumes;

executing said rigid registration algorithm to register said first clinical image volume to each of said plurality of candidate CT image volumes and thereby obtain a plurality of corresponding candidate similarity metrics; and selecting said reference CT image volume from among said plurality of candidate CT image volumes based on a comparison of each of said plurality of corresponding candidate similarity metrics to a desired similarity metric.

12. The method of claim 10, wherein said step of applying said rigid registration algorithm comprises:
executing an affine transform algorithm having a plurality of variables including translation, rotation, scale, and shear;
selecting a similarity metric representing alignment of said reference CT image volume to said first clinical image volume; and
optimizing said variables iteratively until said similarity metric achieves a minimum limit.

13. The method of claim 12, wherein said step of optimizing further comprises:
setting an iteration maximum;
setting a similarity metric minimum; and
halting optimizing after either said iteration maximum equals about thirty or said similarity metric minimum falls below $10^{-5}$.

14. The method of claim 10, wherein said step of applying said smoothing function comprises:
executing a B-spline transform wherein a deformation is defined by a grid of nodes superimposed on said first registration, said B-spline transform having a plurality of variables including node deformation;
selecting a similarity metric representing alignment of said first registration to said first clinical image volume; and
optimizing said plurality of variables iteratively until said similarity metric achieves a minimum limit.

15. The method of claim 14, wherein said step of executing said B-spline transform further comprises:
executing a first stage B-spline transform wherein said grid of nodes comprises a first grid of nodes arrayed at a first spacing distance superimposed on said first registration, said first stage B-spline transform producing an intermediate registration; and
executing a second stage B-spline transform wherein said grid of nodes further comprises a second grid of nodes arrayed at a second spacing distance superimposed on said intermediate registration, wherein said second spacing distance is shorter than said first spacing distance.

16. The method of claim 10, wherein said step of executing said voxelwise intensity algorithm comprises:
executing a deformable image registration transform having a plurality of nonlinear variables;
defining at least a displacement vector at each voxel;
selecting a similarity metric representing alignment of said smoothed registration to said first clinical image volume; and
optimizing said plurality of nonlinear variables iteratively, according to said displacement vector, until said similarity metric achieves a minimum limit.

17. The method of claim 16, wherein said step of optimizing further comprises:
optimizing said plurality of nonlinear variables according to a partial differential equation having a diffeomorphic update step.

18. The method of claim 16, wherein said step of selecting further comprises:
selecting a similarity metric having a variational expression of a mutual information component that is varied according to a local value of an image intensity gradient based at least partially on said displacement vector.

19. A non-transitory computer-readable medium, contents of which cause a computing system to perform a method of creating a synthetic computed-tomography (CT) image volume, said method comprising:
obtaining a first clinical image volume;
retrieving a reference CT image volume;
applying a rigid registration algorithm to register said reference CT image volume to said first clinical image volume and thereby produce a first registration;
applying a smoothing function to said first registration and thereby produce a smoothed registration;
applying a voxelwise intensity algorithm to said smoothed registration and thereby produce said synthetic CT image volume having characteristics correlated to those of said first clinical image volume;
obtaining a second clinical image volume;
deriving a map of attenuation coefficients based on said synthetic CT image volume; and
correcting said second clinical image volume for attenuation based on said map of attenuation coefficients.

20. The non-transitory computer-readable medium of claim 19, wherein said step of applying said rigid registration algorithm comprises:
executing an affine transform algorithm having a plurality of variables including translation, rotation, scale, and shear;
selecting a similarity metric representing alignment of said reference CT image volume to said first clinical image volume; and
optimizing said plurality of variables iteratively until said similarity metric achieves a minimum limit.

21. The non-transitory computer-readable medium of claim 19, wherein said step of applying said smoothing function comprises:
executing a B-spline transform wherein a deformation is defined by a grid of nodes superimposed on said first registration, said B-spline transform having a plurality of variables including node deformation;
selecting a similarity metric representing alignment of said first registration to said first clinical image volume; and
optimizing said plurality of variables iteratively until said similarity metric achieves a minimum limit.

22. The non-transitory computer-readable medium of claim 19, wherein said step of executing said voxelwise algorithm comprises:
executing a deformable image registration transform having a plurality of nonlinear variables;
defining at least a displacement vector at each voxel;
selecting a similarity metric representing alignment of said smoothed registration to said first clinical image volume; and
optimizing said plurality of nonlinear variables iteratively, according to said displacement vector, until said similarity metric achieves a minimum limit.

23. The system of claim 1, further comprising a selection tool configured to select said reference CT image volume from among a plurality of candidate CT image volumes based on a comparison of a desired similarity metric to candidate similarity metrics corresponding to the plurality of candidate CT image volumes.

24. The system of claim 1, wherein the attenuation correction engine is further configured to derive said map of attenuation coefficients.

25. The system of claim 2, further comprising:
a map of attenuation coefficients based on said synthetic CT image volume; and an attenuation correction engine configured to correct attenuation in a second clinical image volume based on said map of attenuation coefficients.

* * * * *